(12) United States Patent
Graves (10) Patent No.: US 7,901,441 B2
(45) Date of Patent: Mar. 8, 2011

(54) METHOD OF USING AN IMAGING CATHETER TO CONDUCT PHOTODYNAMIC PROCEDURES

(75) Inventor: David Micky Graves, Mesa, AZ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1090 days.

(21) Appl. No.: 11/252,761

(22) Filed: Oct. 18, 2005

(65) Prior Publication Data

US 2007/0088195 A1    Apr. 19, 2007

(51) Int. Cl.
*A61B 1/04*    (2006.01)

(52) U.S. Cl. ...... 607/88; 128/898; 604/508; 604/164.11; 600/108

(58) Field of Classification Search .............. 607/88, 607/89; 128/898; 606/2–15; 604/508, 164.11, 604/164.09
See application file for complete search history.

(56) References Cited

U.S. PATENT DOCUMENTS

| | | | |
|---|---|---|---|
| 4,607,622 A * | 8/1986 | Fritch et al. ................. | 600/108 |
| 4,782,819 A | 11/1988 | Adair | |
| 4,830,460 A * | 5/1989 | Goldenberg ................. | 385/118 |
| 5,009,655 A | 4/1991 | Daignault, Jr. et al. | |
| 5,047,627 A | 9/1991 | Yim et al. | |
| 5,098,659 A | 3/1992 | Yim et al. | |
| 5,192,287 A * | 3/1993 | Fournier et al. ............. | 606/139 |
| 5,290,892 A * | 3/1994 | Namdaran et al. .......... | 526/259 |
| 5,311,858 A | 5/1994 | Adair | |
| 5,383,467 A | 1/1995 | Auer et al. | |
| 5,396,880 A | 3/1995 | Kagan et al. | |
| 5,409,453 A | 4/1995 | Lundquist et al. | |
| 5,439,000 A | 8/1995 | Gunderson et al. | |
| 5,445,608 A * | 8/1995 | Chen et al. .................. | 604/20 |
| 5,601,087 A | 2/1997 | Gunderson et al. | |

(Continued)

FOREIGN PATENT DOCUMENTS

WO    WO 94/11040 A1    5/1994

(Continued)

OTHER PUBLICATIONS

International Search Report and Written Opinion of the International Searching Authority, dated Apr. 25, 2007, issued in PCT/US2006/037327.

*Primary Examiner* — Henry M Johnson, III
*Assistant Examiner* — Jeffrey B Lipitz
(74) *Attorney, Agent, or Firm* — Finnegan, Henderson, Farabow, Garrett & Dunner, LLP (57) ABSTRACT

A method of using an imaging catheter for activating a photodynamic agent is provided. The method generally includes four steps. First, an imaging catheter including a fiber optic cable is inserted within a body cavity or vessel. The fiber optic cable has a first end (e.g., proximal end) and a second end (e.g., distal end), and is configured to transmit electromagnetic irradiation from its first end to its second end and to transmit an image from its second end to its first end. Second, an image of a site of interest (e.g., the location of an aneurysm) within the body cavity or vessel is observed using the fiber optic cable. Third, a suitable photodynamic agent is applied to the site of interest. Fourth, the fiber optic cable is used to deliver a selected wavelength or wavelength range of electromagnetic energy to the site to thereby activate the photodynamic agent.

20 Claims, 5 Drawing Sheets

U.S. PATENT DOCUMENTS

| | | | |
|---|---|---|---|
| 5,725,522 A | 3/1998 | Sinofsky | |
| 5,779,643 A | 7/1998 | Lum et al. | |
| 5,824,026 A | 10/1998 | Diaz | |
| 5,993,378 A | 11/1999 | Lemelson | |
| 6,081,740 A * | 6/2000 | Gombrich et al. | 600/424 |
| 6,296,608 B1 | 10/2001 | Daniels et al. | |
| 6,454,790 B1 * | 9/2002 | Neuberger et al. | 607/88 |
| 6,654,630 B2 | 11/2003 | Zuluaga et al. | |
| 2001/0029328 A1 * | 10/2001 | Crowley | 600/372 |
| 2001/0029373 A1 * | 10/2001 | Baker et al. | 606/49 |
| 2002/0009275 A1 * | 1/2002 | Williams et al. | 385/123 |
| 2003/0028227 A1 * | 2/2003 | Neuberger et al. | 607/88 |
| 2003/0097116 A1 * | 5/2003 | Putz | 604/509 |
| 2003/0187427 A1 * | 10/2003 | Gatto | 606/15 |
| 2003/0216718 A1 * | 11/2003 | Hamblin et al. | 606/8 |
| 2004/0024349 A1 * | 2/2004 | Flock et al. | 604/22 |
| 2004/0093044 A1 * | 5/2004 | Rychnovsky et al. | 607/88 |
| 2005/0112131 A1 * | 5/2005 | Pogue et al. | 424/178.1 |
| 2010/0198009 A1 | 8/2010 | Farr et al. | |

FOREIGN PATENT DOCUMENTS

| | | |
|---|---|---|
| WO | 9945838 A | 9/1999 |
| WO | WO 99/45847 A1 | 9/1999 |
| WO | WO 01/89598 A2 | 11/2001 |
| WO | 0207629 A | 1/2002 |
| WO | WO 03/082394 A1 | 10/2003 |
| WO | WO 2004/007012 A2 | 1/2004 |
| WO | WO 2004/012805 A2 | 2/2004 |

* cited by examiner

METHOD OF USING AN IMAGING CATHETER TO CONDUCT PHOTODYNAMIC PROCEDURES

FIELD OF THE INVENTION

The present invention relates to medical procedures, and in particular to a method of using an imaging catheter to apply electromagnetic energy to a site of interest to carry out a photodynamic procedure.

BACKGROUND OF THE INVENTION

An aneurysm is a localized, pathological, blood-filled dilatation of a blood vessel caused by a disease or weakening of the vessel. The present state of the art in filling aneurysms requires self-curing polymers. A self-curing polymer needs to be rapidly delivered to an aneurysm to ensure that complete filling occurs before the polymer cures and no longer flows. In some instances, the polymer may cure and remain affixed to a polymer deliver device (e.g., a delivery catheter), possibly gluing the delivery device to the anatomy. This could cause injury to the patient upon removal of the delivery device from the anatomy. Alternatively, the device may need to be severed near its distal end portion, leaving the distal end portion of the device adhered in the anatomy.

To reduce the risks associated with the curing polymers, a need exists for an improved method of treating aneurysms and other diseases.

SUMMARY OF THE INVENTION

The present invention offers various methods of using an imaging catheter, which is capable of imaging a site of interest, for the additional purpose of delivering a selected wavelength or wavelength range of electromagnetic energy to carry out a photodynamic procedure.

In accordance with one aspect, the invention is a method of using an imaging catheter for curing a photodynamic polymer/adhesive. The method generally includes four steps. First, an imaging catheter including a fiber optic cable is inserted within a body cavity or vessel. The fiber optic cable has a first end (e.g., proximal end) and a second end (e.g., distal end), and is configured to transmit electromagnetic irradiation (including both visible and non-visible light) from its first end to its second end and to transmit an image from its second end to its first end. Second, an image of a site of interest (e.g., the location of an aneurysm) within the body cavity or vessel is observed using the fiber optic cable. Third, a suitable photodynamic polymer/adhesive material is applied to the site of interest. Fourth, the fiber optic cable is used to deliver a selected wavelength or wavelength range of electromagnetic energy to the site of interest to thereby cure the photodynamic polymer/adhesive deposited thereon.

Accordingly, the imaging catheter including the fiber optic cable may be used to observe the site of interest prior to and during delivery of a photodynamic polymer/adhesive to the site of interest, and also after the polymer/adhesive has been cured at the site of interest. Additionally, the imaging catheter is used to photodynamically cure the polymer/adhesive at the site of interest. In one preferred embodiment, any delivery device used to deliver the polymer/adhesive to the site of interest is removed therefrom prior to delivering the electromagnetic energy to cure the polymer/adhesive. Therefore, there is little risk of inadvertently adhering the delivery device to the site of interest and causing injury to the patient.

In accordance with another aspect, the present invention provides a method of using an imaging catheter for administering a photodynamic therapy. The method generally includes four steps. First, an imaging catheter including a fiber optic cable is inserted within a body cavity or vessel. Second, an image of a site of interest within the body cavity or vessel is observed using the fiber optic cable. Third, a suitable photodynamic therapeutic agent is delivered to the site of interest. Fourth, the fiber optic cable is used to deliver a selected wavelength or wavelength rage of electromagnetic energy to the photodynamic agent at the site of interest to thereby activate the photodynamic therapeutic agent.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
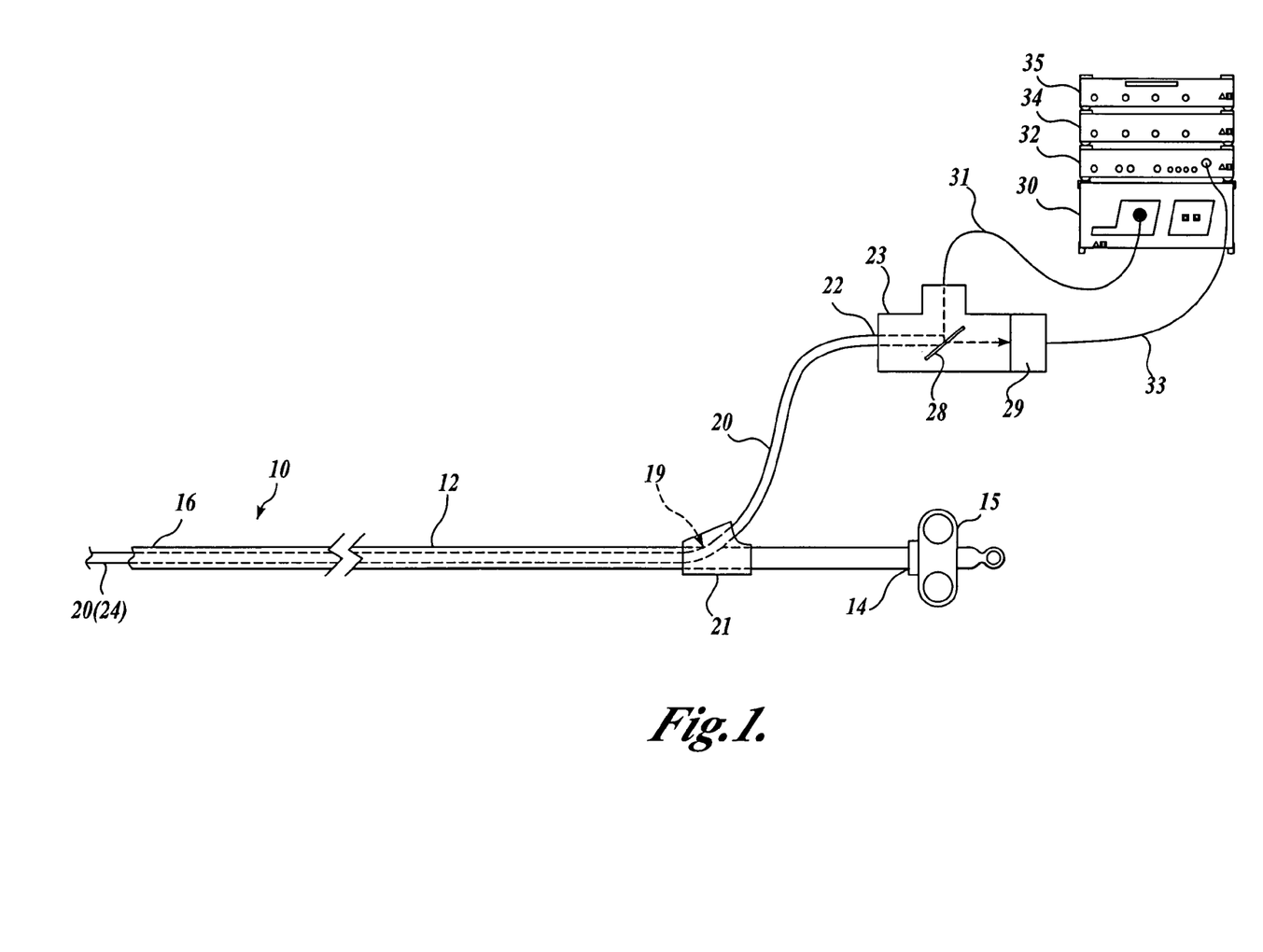
FIG. 1 is a block diagram illustrating an imaging catheter suitable for use in a method in accordance with an embodiment of the present invention, together with related equipment.

FIG. 1 illustrates one possible embodiment of an imaging catheter 10 formed in accordance with the present invention. The catheter 10 includes an elongated catheter tube 12 having a proximal end 14 and a distal end 16. The catheter tube 12 is formed of any suitable flexible material including, but not limited to, extruded plastic such as polytetrafluoroethylene (PTFE, Teflon®), polyether block amide, nylon, or a combination or blend of these. In the illustrated embodiment, the catheter 10 is steerable, and includes one or more steering cables (not shown) extending substantially throughout the length of the catheter tube 12. As known in the art, a distal end of the steering cable is secured at or adjacent to the distal end 16 of the catheter tube, while a proximal end thereof is secured to a handle portion 15 of the catheter. Similar to manipulating a puppet, a physician can manipulate the handle portion 15 to pull or release the steering cable(s) to thereby bend or release the distal end 16 of the catheter tube 12 in order to maneuver the catheter 10 through a body cavity or vessel.

Figure 2:
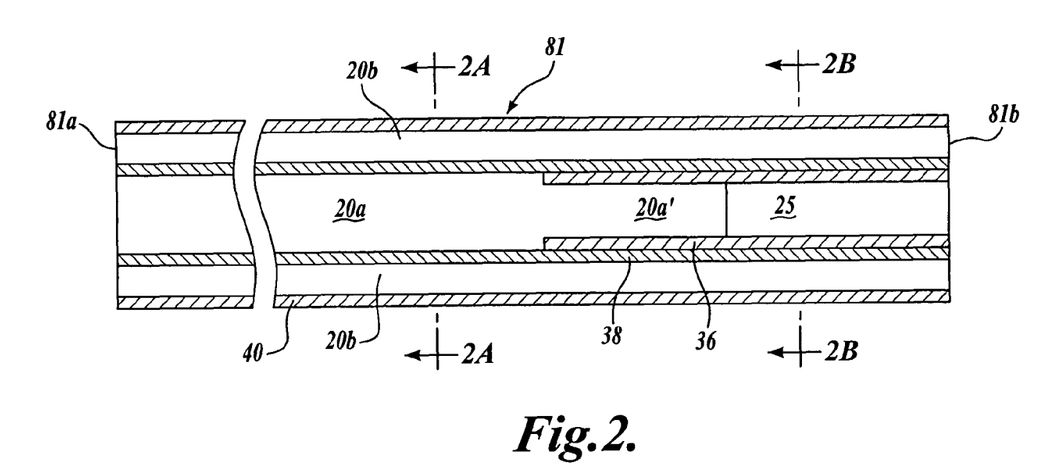
FIG. 2 is a longitudinal cross-sectional view of a fiber optic cable suitable for use in a method in accordance with an embodiment of the present invention.
Figure 2A:
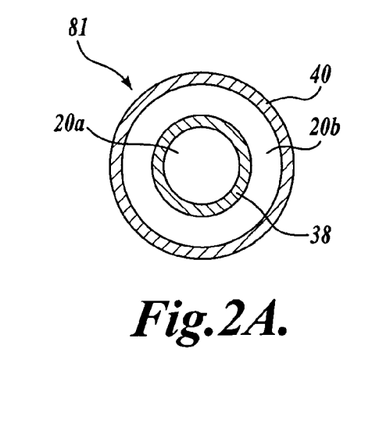
FIGS. 2A and 2B are cross-sectional views taken along lines A-A and B-B, respectively, of the fiber optic cable of FIG. 2.
Figure 2B:
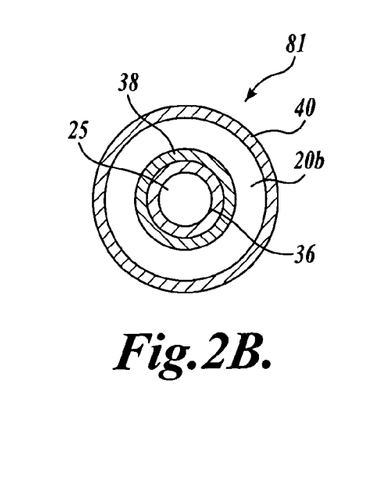

The catheter 10 includes a fiber optic cable 20 having a proximal end 22 and a distal end 24, which extends at least partially along the length of the catheter tube 12. To this end, the illustrated embodiment as shown in FIG. 1 includes a breakout unit 21 configured to receive and combine the catheter tube 12 and the fiber optic cable 20. As will be apparent, in this embodiment, an outer wall of the catheter tube 12 includes an opening 19 through which the fiber optic cable 20 enters into the catheter tube 12 so as to extend through and within the catheter tube 12. The fiber optic cable 20 is configured to transmit illumination light, and also any wavelength or wavelength range of electromagnetic energy (e.g., UV light) selected for use in a photodynamic procedure, from its proximal end 22 to the distal end 24. As used herein, the electromagnetic energy or electromagnetic irradiation includes both visible and non-visible light (such as UV or infrared light) that can be carried by the fiber optic cable 20 to perform a selected photodynamic procedure. The fiber optic cable 20 is also configured to transmit an image from its distal end 24 to the proximal end 22. In the illustrated embodiment, as best shown in FIG. 2, the fiber optic cable 20 includes one or more centrally extending coherent imaging fibers 20a and one or more circumferentially extending irradiation fibers 20b (which may not be coherent) that generally surround the one or more imaging fibers 20a. Further, an objective lens 25 is attached to the distal end of the one or more imaging fibers 20a.

Still referring to FIG. 1, the proximal end 22 of the fiber optic cable 20 may be connected to an eyepiece 23. The eyepiece 23 includes a light splitter 28 and a camera (or image sensor) 29. During imaging, the light splitter 28 receives illumination light from a light source 30 through a cable 31. The light from the light splitter 28 is coupled to the one or more irradiation fibers 20b in the fiber optic cable 20 for delivery to the distal end 24 thereof in order to illuminate the imaged area. An image from the distal end 24 of the fiber optic cable 20 is transmitted through the one or more imaging fibers 20a in the fiber optic cable 20 to the proximal end 22 thereof, and through the light splitter 28 within the eyepiece 23 to the camera (or image sensor) 29. The image is then processed and supplied from the camera (or image sensor) 29 via a cable 33 to a camera control unit 32 coupled to a display (not shown) that displays an image of the viewed area. Additionally, the eyepiece 23 permits direct visualization of the viewed area. Still further, a picture-in-picture unit 34 and a DVD, video tape, or equivalent recorder 35 may be provided to allow a physician to view more than one image at a time on the display as well as to record images for future review.

During a photodynamic procedure, a selected wavelength or wavelength range of electromagnetic energy (e.g., UV light) is provided from the light source 30 (if it is configured to generate electromagnetic energy at multiple wavelengths or wavelength ranges) or from another electromagnetic energy source. The generated wavelength or wavelength range of electromagnetic energy is then transmitted through the irradiation fibers 20b of the fiber optic cable 20 for delivery to the distal end 24 thereof in order to carry out a photodynamic procedure, as will be more fully described below.

FIG. 2 illustrates an embodiment of a fiber optic cable 20 suitable for use in the present invention. In the illustrated embodiment, the objective lens 25 and the distal end of the one or more imaging fibers 20a are connected by a transparent adhesive. Further, a non-transparent adhesive is applied on the radially outer surface of the lens 25 and also on the radially outer surface of the distal portion 20a' of the one or more imaging fibers 20a, and a first tube or sheath 36 is slid thereover to cure the adhesive and to further bond the lens 25 to the distal end of the one or more imaging fibers 20a. Then, a non-transparent adhesive is applied on the radially outer surface of the first tube 36, and a second tube 38 is slid over both the first tube 36 and the one or more imaging fibers 20a. The one or more irradiation fibers 20b are arranged radially outward of the second tube or sheath 38 and are impregnated with a transparent adhesive. A protecting tube or sheath 40 is then slid over the length of the impregnated irradiation fibers 20b. While the illustrated embodiment includes the lens 25 to focus an image for transmission through the one or more imaging fibers 20a, a lens may be omitted in some applications. For example, the distal ends of the one or more imaging fibers 20a themselves may be tapered so as to internally focus an image without an additional lens.

In one embodiment, the diameter of the lens 25 is 0.35' mm and the overall diameter of the fiber optic cable 20 is 0.78 mm, though the various dimensions of the fiber optic cable 20 are not so limited as should be apparent to one skilled in the art. A suitable fiber optic cable of this type for use in the present invention is available from POLYDIAGNOST GmbH of Germany (www.polydiagnost.com). It should be understood that other types of fiber optic cables having capabilities to transmit both an image and electromagnetic energy (including both visible and non-visible ranges) may be used, as will be apparent to one skilled in the art.

Figure 3A:
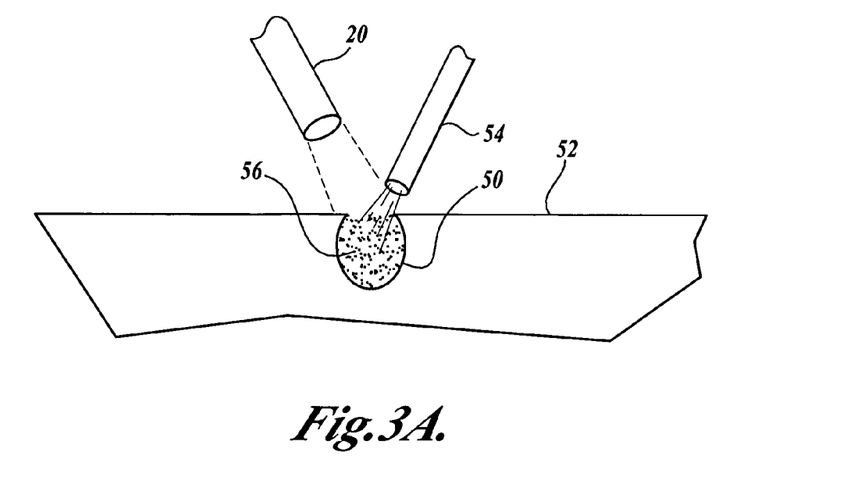
FIGS. 3A and 3B illustrate a method of filling an aneurysm with a photodynamic polymer/adhesive and curing the polymer/adhesive with electromagnetic energy using an imaging catheter in accordance with one application of the present invention.

The present invention offers various methods of using an imaging catheter to carry out a photodynamic procedure. FIG. 3A illustrates a method of filling an aneurysm 50 found in a vessel wall or intestinal wall 52. First, the imaging catheter including the fiber optic cable 20 is inserted into a body cavity or vessel until the distal end 24 of the fiber optic cable 20 is placed near the aneurysm 50. At this time, the imaging catheter is used for imaging purposes so that a physician can visually observe and assess the aneurysm 50. Then, a suitable photodynamic agent delivery device 54 (or the imaging catheter itself) is used to fill the aneurysm 50 with a photodynamic agent 56, such as a polymer/adhesive. Examples of photodynamic polymers/adhesives suitable for use in a method in accordance with the present invention include acrylics, silicones, cyanoacrylates, fibrinogen glue, chlorin(e6) protein conjugates, or other biocompatible substances that can be cured within the body by application of electromagnetic energy. The polymer/adhesive delivery operation may be conducted while the physician continues to observe the site using the fiber optic cable 20. In one embodiment, the photodynamic agent delivery device 54 is passed through an additional lumen extending through the imaging catheter 10. If the polymer/adhesive is inadvertently deposited on a wrong location, or is deposited in excess, any undesirable polymer/adhesive can be removed, for example by suction (e.g., by using an aspiration catheter). Thus, it can be ensured that the right amount of polymer/adhesive is correctly deposited on the site of interest. In the illustrated embodiment, a suitable amount of photodynamic agent 56 is deposited to fill the aneurysm 50. Preferably, the photodynamic agent delivery device 54 is then removed from the site.

Figure 3B:
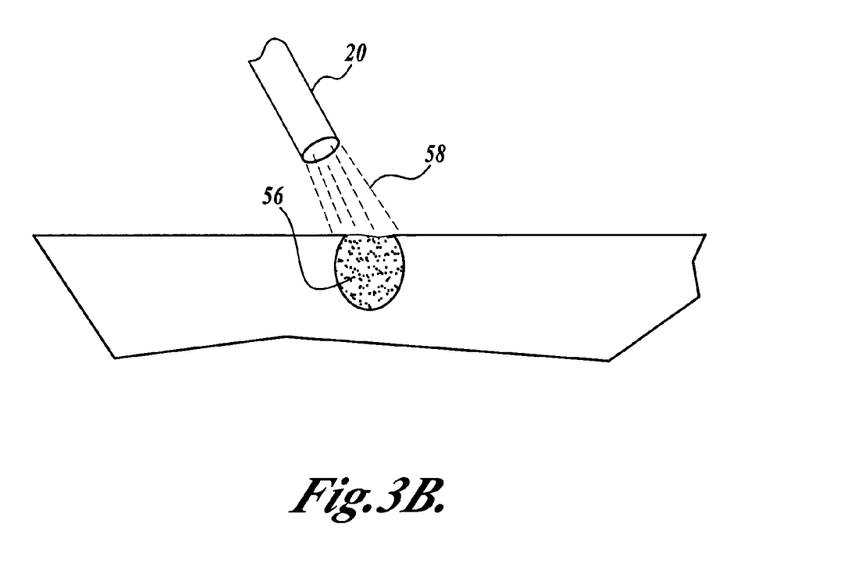

Thereafter, referring to FIG. 3B, the fiber optic cable 20 is used to carry out a photodynamic procedure. Specifically, the fiber optic cable 20 is used to irradiate the photodynamic agent 56 with a wavelength or wavelength range of electromagnetic energy 58 selected to cure the photodynamic agent 56 (e.g., UV light). Since the photodynamic agent delivery device 54 has been removed, there is little risk of inadvertently adhering the delivery device 54 to the site.

Figure 4A:
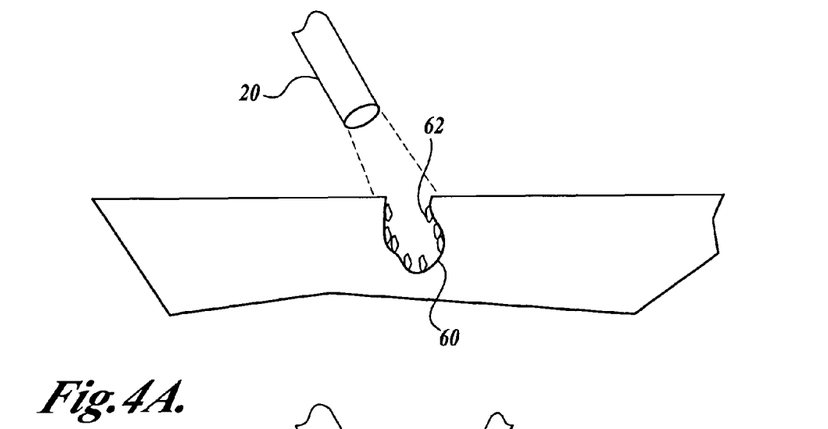
FIGS. 4A-4C illustrate a method of filling or closing a deep tissue void with a photodynamic polymer/adhesive and curing the polymer/adhesive with electromagnetic energy using an imaging catheter in accordance with another application of the present invention.
Figure 4B:
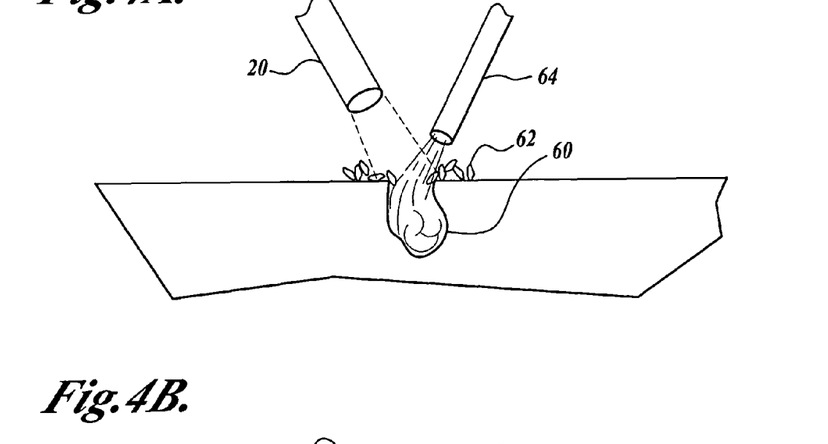

FIG. 4A illustrates another example of a photodynamic procedure performed in accordance with the present invention, involving closing a deep tissue void 60 in the intestinal wall. As in FIG. 3A, the fiber optic cable 20 is first introduced via the imaging catheter to observe the deep tissue void 60. Then, referring to FIG. 4B, a suitable catheter 64 (which may be the imaging catheter itself) is introduced to flush or vacuum out any debris 62 from the tissue void 60. At this time, the physician may observe the flushing or vacuuming operation using the fiber optic cable 20 to visually confirm that all debris 62 are removed from the tissue void 60.

Figure 4C:
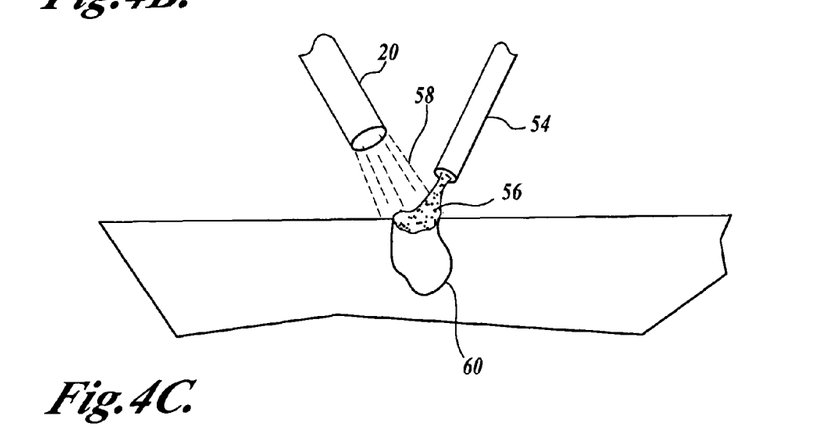

Thereafter, referring to FIG. 4C, a photodynamic agent delivery catheter 54 (or the imaging catheter itself) is used to deposit a photodynamic agent 56, such as an adhesive/polymer, at the opening of the tissue void 60 so as to prevent contamination (debris, etc.) from entering or re-entering the tissue void 60. Alternatively, the photodynamic agent 56 may be deposited to completely fill the tissue void 60. Any excess or improperly-placed adhesive/polymer can be removed using vacuum, etc. to ensure that the right amount of polymer/adhesive is deposited at the site of interest (e.g., at the opening of the deep tissue void 60). Preferably, the photodynamic agent delivery catheter 54 is then removed from the site. Thereafter, the fiber optic cable 20 is used to irradiate the photodynamic agent 56 with a selected wavelength or wavelength range of electromagnetic energy 58 (e.g., UV light) to thereby cure the photodynamic agent 56 and to close off the tissue void 60.

The photodynamic procedure involving the use of an imaging catheter to cure a photodynamic polymer/adhesive, as described above, can be applied in various other settings and procedures also. For example, this type of photodynamic procedure can be used to occlude a passageway or vessel, encapsulate tissue, etc.

FIGS. 5A-5D illustrate yet another example of a method in accordance with the present invention, involving depositing a different photodynamic agent, such as a therapeutic agent, at a site of interest and activating the agent using an imaging catheter of the present invention. As is known in the art, healthy tissue will absorb certain therapeutic agents at a relatively known rate. A cancerous or diseased tissue will often absorb the same therapeutic agents at a faster rate. This is in part due to the nature of the cancerous or diseased tissue having a higher metabolic rate or rate of cell replication. This difference in rate of absorption of the therapeutic agent between the healthy and unhealthy tissue can be exploited.

Figures 5A, 5B, 5C, 5D:
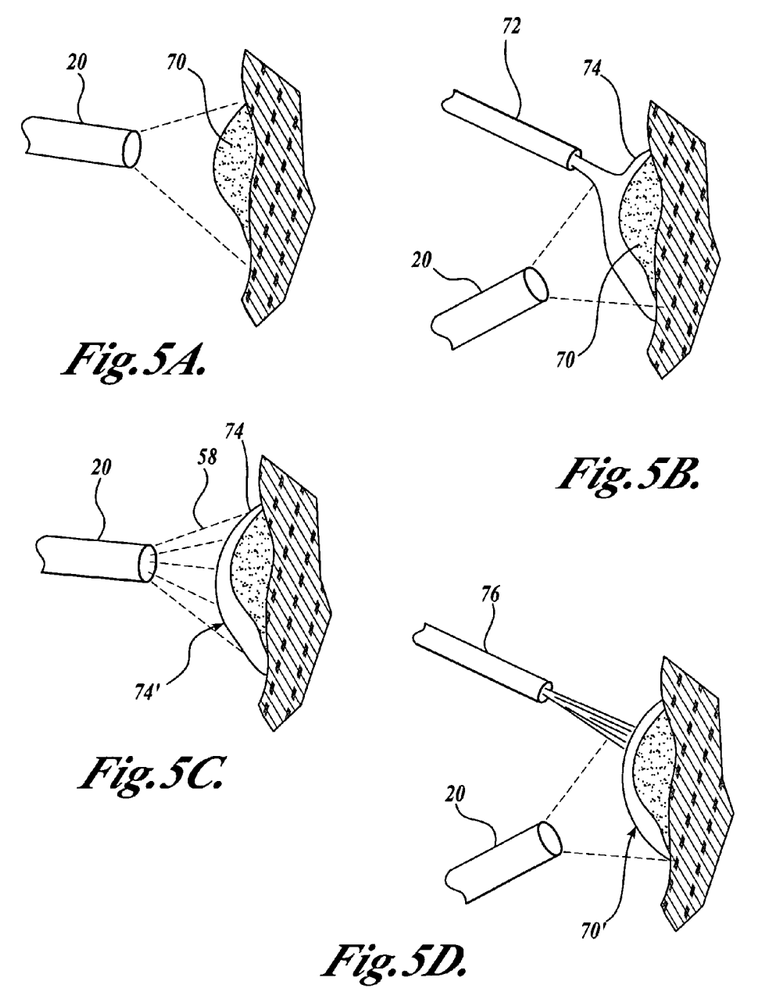
FIGS. 5A-5D illustrate a method of treating a site by applying a photodynamic therapeutic agent thereto and activating the agent with electromagnetic energy using an imaging catheter in accordance with yet another application of the present invention.

Specifically, in FIG. 5A, the fiber optic cable 20 is inserted through an imaging catheter and is used to observe a site to be treated 70 (e.g., cancerous tissue). In FIG. 5B, a suitable delivery catheter 72 is used to deliver (e.g., spray, inject, etc.) a photodynamic therapeutic agent 74 to the site 70. Multiple agents may be used to prepare, clear, or prime tissue to be treated depending on a particular procedure. In one embodiment, the therapeutic agent is administered in a dose that is lethal to the unhealthy tissue and at the same time non-lethal to the healthy tissue so that when the therapeutic agent is activated only the unhealthy tissue will be destroyed. Examples of a photodynamic therapeutic agent suitable for use in a method in accordance with the present invention include (BPD-MA) benzoponphyrin derivative monoacid ring A and (SnET2) tinethyl etiopurpurin, aminolevulinic acid, porfimer sodium, and lutetium texaphyrin. The physician can observe the delivery of the photodynamic therapeutic agent 74 using the fiber optic cable 20. Preferably, the delivery catheter 72 is removed prior to activation by the imaging catheter.

Thereafter, in FIG. 5C, the fiber optic cable 20 is used to irradiate the site to which the therapeutic agent has been applied 74', with a selected wavelength or wavelength range of electromagnetic energy 58 for a predefined time to thereby activate the photodynamic therapeutic agent 74. Provided that an applied dose of the photodynamic therapeutic agent 74 is lethal to the unhealthy tissue and non-lethal to the healthy tissue, when the photodynamic therapeutic agent 74 is activated with the electromagnetic energy applied, the lethal dose and non-lethal dose reactions occur simultaneously and the unhealthy tissue will be destroyed.

Finally, in FIG. 5D, the fiber optic cable 20 can be again used to observe the treated site 70' to visually confirm the effectiveness of the treatment. Additionally, a suitable catheter 76 may be inserted to apply a termination agent, or for rinsing the treated site 70' with a fluid (water, $CO_2$, etc.).

The present invention further offers various kits that are specifically adapted for carrying out the methods of the present invention, as described above. For example, a kit adapted for use in filling a void within a patient's body may be provided. The kit includes generally two elements: a catheter having a lumen therein that is adapted to receive a fiber optic cable, and a photodynamic agent that is delivered through a second lumen of the catheter to a site of interest and activated upon exposure to the electromagnetic irradiation from the fiber optic cable. In one embodiment, the catheter and the fiber optic cable may be integrally formed. As another example, a kit adapted for use in conducting a photodynamic therapy within a patient's body is provided. This kit also consists of generally two elements: a catheter having a lumen therein that is adapted to receive a fiber optic cable, and a photodynamic therapeutic agent that is delivered through a second lumen of the catheter to a site of interest and activated upon exposure to the electromagnetic irradiation from the fiber optic cable.

Figure 6:
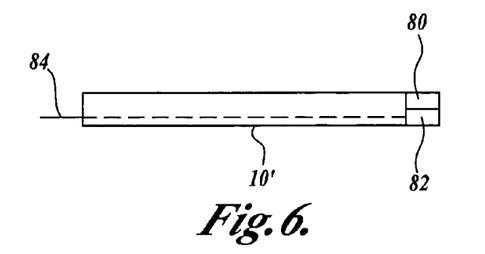
FIG. 6 illustrates an alternative embodiment of a catheter including an LED light source, suitable for use in a method of the present invention.

While the preferred embodiments of the invention have been illustrated and described, it will be appreciated that various changes can be made therein without departing from the scope of the invention. For example, while the embodiments described above use a fiber optic cable as a light source, in other embodiments, other light sources such as an LED placed at a distal end of a catheter may be used. Specifically referring to FIG. 6, a catheter 10' includes a distal end to be inserted within a body cavity or vessel, and a light source 80, such as an LED, is placed at or near the distal end. The catheter 10' may be used in a method of curing a photodynamic polymer/adhesive and/or a method of administering a photodynamic therapy, as described in detail above, except that the catheter 10' does not have the imaging (or image observing) capability, unless a separate imager is additionally provided. Such an imager may comprise, for example, a camera 82 provided at a distal end of a signal cable 84. The camera may be a CCD, CMOS, pin hole, photo diode, or any other type of camera. An image obtained by the camera 82 is transmitted via the signal cable 84 to its proximal end and to an image processor (not shown) such that the image from the camera 84 can be received and processed.

The embodiments of the invention in which an exclusive property or privilege is claimed are defined as follows:

1. A method of administering a photodynamic therapy, comprising:
   (a) inserting an imaging catheter comprising a light source and an imaging device within a body cavity or vessel, the imaging catheter having a first end and a second end, the light source being configured to deliver electromagnetic irradiation to a site of interest, and the imaging device being configured to obtain an image from the site of interest;
(b) inserting a photodynamic agent delivery catheter within the body cavity or vessel and advancing the delivery catheter to the site of interest;
(c) delivering a photodynamic agent to the site of interest;
(d) removing the photodynamic agent delivery catheter from the site of interest; and;
(e) using the light source to deliver electromagnetic energy to the photodynamic agent at the site of interest to activate the photodynamic agent, wherein the imaging catheter remains in the body cavity or vessel when the photodynamic agent delivery catheter is removed from the site of interest, and steps (b) through (d) occur while maintaining the imaging catheter within the body cavity or vessel for continually obtaining the image from the site of interest.

2. The method of claim 1, wherein the step (e) occurs after the photodynamic agent delivery catheter is removed from the site of interest.

3. The method of claim 1, wherein either step (a) or step (e) includes inserting the light source within a first lumen of the imaging catheter, and step (c) including delivering the photodynamic agent through a second lumen of the imaging catheter.

4. The method of claim 1, wherein step (a) includes inserting the imaging catheter having a fiber optic cable with a diameter less than 1 mm.

5. The method of claim 1, wherein the photodynamic agent includes a photodynamic polymer/adhesive.

6. The method of claim 1, wherein prior to step (e), removing photodynamic agent deposited away from the site of interest or in excess to the site of interest.

7. The method of claim 1, wherein prior to step (b), removing debris present at the site of interest.

8. The method of claim 1, wherein during steps (b) through (e), the imaging device is configured to continually obtain the image from the site of interest.

9. The method of claim 1, wherein during steps (b) through (e), the light source and the imaging device are both maintained within the imaging catheter.

10. The method of claim 1, wherein during step (a), a single fiber optic cable comprises both the light source and the imaging device.

11. A method of administering a photodynamic therapy to an aneurysm or a deep tissue void, comprising:
(a) inserting a an imaging catheter comprising a light source and an imaging device within a body cavity or vessel to locate the aneurysm or the deep tissue void, the catheter having a first end and a second end, the light source being configured to deliver electromagnetic irradiation to a site of interest, and the imaging device being configured to obtain an image from the site of interest;
(b) inserting a delivery catheter within the body cavity or vessel, and advancing the delivery catheter to the site of interest;
(c) delivering a photodynamic polymer/adhesive to the site of interest through the delivery catheter;
(d) removing the delivery catheter from the site of interest; and
(e) using the light source to deliver electromagnetic energy to the photodynamic polymer/adhesive at the site of interest to activate the photodynamic polymer/adhesive after the inserted delivery catheter is removed, wherein the imaging catheter remains in the body cavity or vessel when the delivery catheter is removed from the site of interest, and steps (c) through (e) occur while maintaining the imaging catheter within the body cavity or vessel for continually obtaining the image from the site of interest.

12. The method of claim 11, wherein prior to step (e), removing photodynamic agent deposited away from the site of interest or in excess to the site of interest.

13. The method of claim 11, wherein prior to step (b), removing debris present at the site of interest.

14. The method of claim 11, wherein during steps (b) through (e), the imaging device is configured to continually obtain the image from the site of interest.

15. The method of claim 11, wherein during steps (b) through (e), the light source and the imaging device are both maintained within the imaging catheter.

16. A method of administering a photodynamic therapy to an aneurysm or a deep tissue void, comprising:
(a) inserting a an imaging catheter comprising a light source and an imaging device within a body cavity or vessel to locate the aneurysm or the deep tissue void, the imaging catheter having a first end and a second end, the light source being configured to deliver electromagnetic irradiation to a site of interest, and the imaging device being configured to obtain an image from the site of interest;
(b) inserting a delivery catheter within the body cavity or vessel, and advancing the delivery catheter to the site of interest;
(c) delivering a photodynamic polymer/adhesive to the site of interest through the delivery catheter to fill the aneurysm or the deep tissue void with the photodynamic polymer/adhesive;
(d) removing the delivery catheter while maintaining the imaging catheter within the body cavity or vessel; and
(e) using the light source to deliver electromagnetic energy to the photodynamic polymer/adhesive at the site of interest, wherein steps (c) through (e) occur while maintaining the imaging catheter from within the body cavity or vessel for continually obtaining the image from the site of interest.

17. The method of claim 16, wherein prior to step (e), removing photodynamic agent deposited away from the site of interest or in excess to the site of interest.

18. The method of claim 16, wherein the photodynamic polymer/adhesive delivered in step (c) is selected from the group consisting of acrylics, silicones, cyanoacrylates, fibrinogen glue, and chlorine(e6) protein conjugates.

19. The method of claim 16, wherein during steps (b) through (e), the imaging device is configured to continually obtain the image from the site of interest.

20. The method of claim 16, wherein during steps (b) through (e), the light source and the imaging device are both maintained within the imaging catheter.

* * * * *

UNITED STATES PATENT AND TRADEMARK OFFICE
CERTIFICATE OF CORRECTION

| | | |
|---|---|---|
| PATENT NO. | : 7,901,441 B2 | Page 1 of 1 |
| APPLICATION NO. | : 11/252761 | |
| DATED | : March 8, 2011 | |
| INVENTOR(S) | : Graves | |

It is certified that error appears in the above-identified patent and that said Letters Patent is hereby corrected as shown below:

Claim 11, col. 7, line 49, "inserting a an imaging catheter" should read
--inserting an imaging catheter--.

Claim 16, col. 8, line 24 "inserting a an imaging catheter" should read
--inserting an imaging catheter--.

Signed and Sealed this
Tenth Day of May, 2011

David J. Kappos
*Director of the United States Patent and Trademark Office*